US011300696B2

(12) United States Patent
Yokoi et al.

(10) Patent No.: US 11,300,696 B2
(45) Date of Patent: Apr. 12, 2022

(54) RADIATION IMAGING DEVICE AND PHOTON COUNTING TYPE DETECTOR CALIBRATION METHOD

(71) Applicant: Hitachi, Ltd., Tokyo (JP)

(72) Inventors: Kazuma Yokoi, Tokyo (JP); Isao Takahashi, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 0 days.

(21) Appl. No.: 16/797,609

(22) Filed: Feb. 21, 2020

(65) Prior Publication Data

US 2020/0278461 A1 Sep. 3, 2020

(30) Foreign Application Priority Data

Feb. 28, 2019 (JP) .............................. JP2019-035465

(51) Int. Cl.
  *G06T 1/00* (2006.01)
  *G01T 7/00* (2006.01)
  *G01T 1/16* (2006.01)
  *A61B 6/00* (2006.01)
(52) U.S. Cl.
  CPC ............ *G01T 7/005* (2013.01); *A61B 6/4241* (2013.01); *A61B 6/585* (2013.01); *G01T 1/16* (2013.01); *A61B 6/5258* (2013.01)
(58) Field of Classification Search
  CPC ..... A61B 6/032; A61B 6/4241; A61B 6/5258; A61B 6/585; G01T 1/16; G01T 1/171; G01T 7/005
  See application file for complete search history.

(56) References Cited

U.S. PATENT DOCUMENTS

| 2004/0156480 | A1* | 8/2004 | Gerwin | A61B 6/583 378/207 |
| 2014/0314211 | A1 | 10/2014 | Zou et al. | |
| 2015/0160355 | A1* | 6/2015 | Wang | A61B 6/585 378/19 |
| 2019/0313993 | A1* | 10/2019 | Zhou | A61B 6/502 |

FOREIGN PATENT DOCUMENTS

JP 6386997 B2 9/2018

* cited by examiner

*Primary Examiner* — Dani Fox
(74) *Attorney, Agent, or Firm* — Crowell & Moring LLP

(57) ABSTRACT

A radiation imaging device capable of reducing the number of measurement times of calibration data used in pile up correction while maintaining the accuracy of the pile up correction. The radiation imaging device has a photon counting type detector to output an electric signal corresponding to energy of an incident radiation photon. The radiation imaging device includes: an extraction unit that extracts a component by the number of pile ups from a material spectrum, as a photon energy spectrum, obtained by detecting a radioactive ray transmitted through a calibration member, formed by combining plural basal substances having different radiation attenuation coefficients, with the photon counting type detector; and a synthesis unit that generates a calibrated equivalent spectrum, as a photon energy spectrum to be collated with an imaging spectrum obtained by imaging a subject by synthesizing the components by the number of pile ups based on the imaging spectrum.

7 Claims, 8 Drawing Sheets

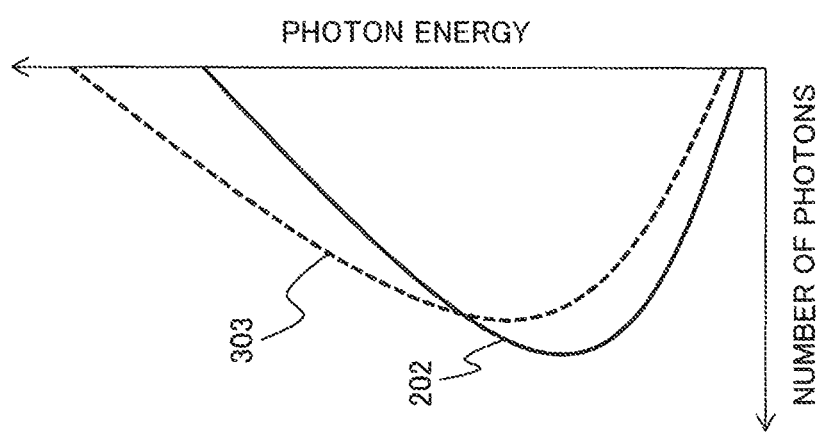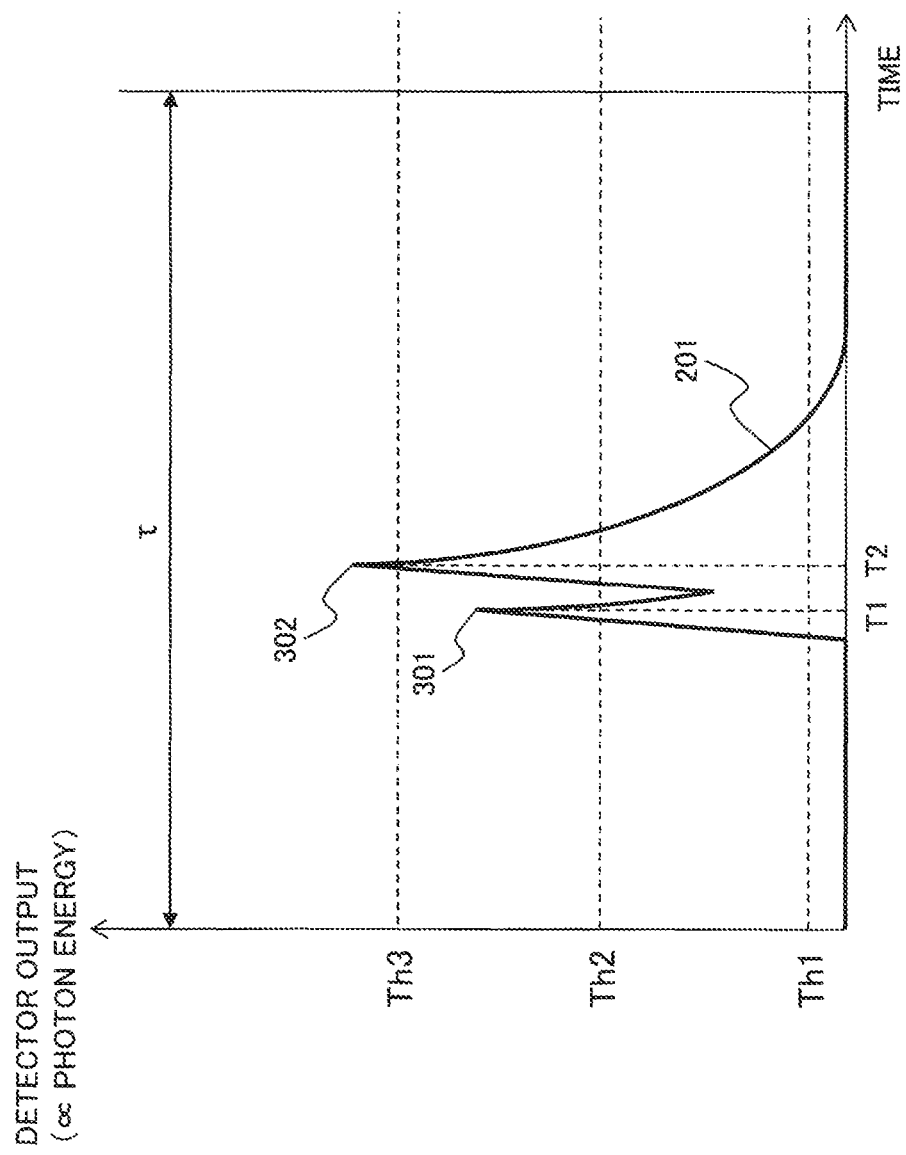

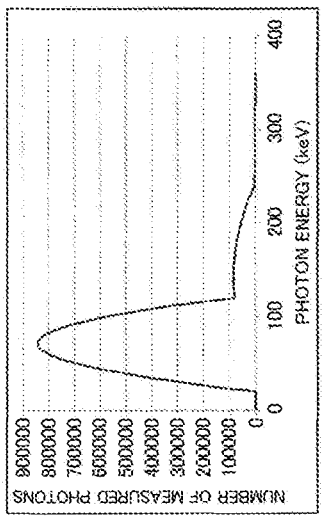 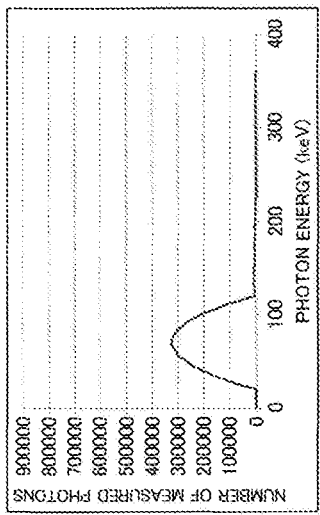 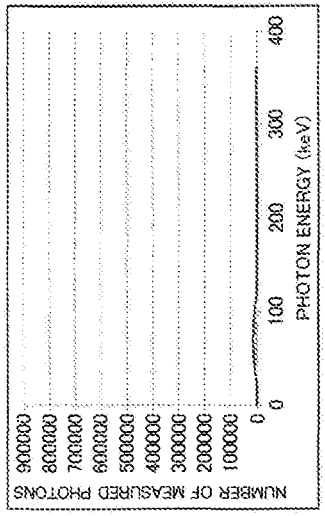
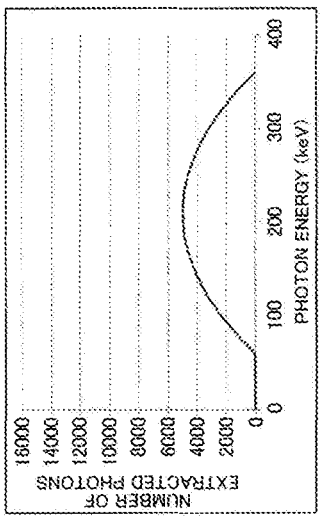 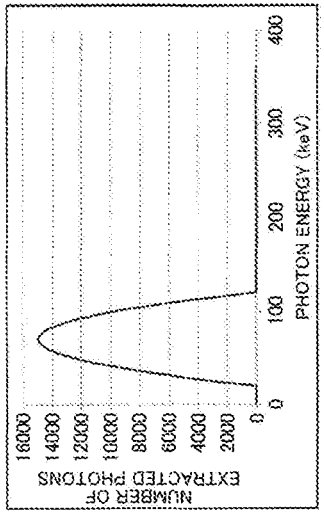
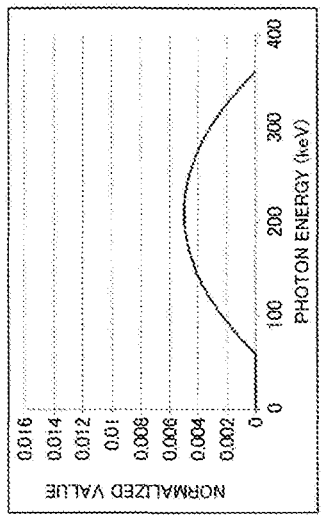 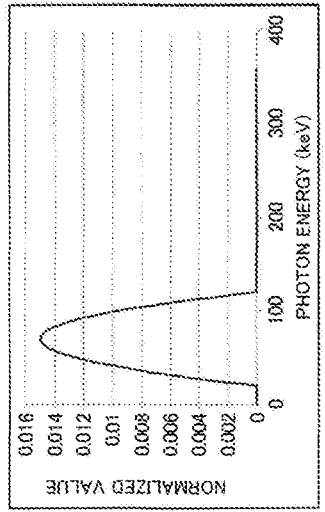

RADIATION IMAGING DEVICE AND PHOTON COUNTING TYPE DETECTOR CALIBRATION METHOD

CLAIM OF PRIORITY

The present application claims priority from Japanese Patent Application JP 2019-035465 filed on Feb. 28, 2019, the content of which are hereby incorporated by references into this application.

BACKGROUND OF THE INVENTION

The present invention relates to a radiation imaging device having a photon counting type detector, and relates to a photon counting type detector calibration method.

BACKGROUND ART

Development of a PCCT (Computed Tomography) device having a photon counting type detector which is a detector using a photon counting method is advanced. The photon counting type detector is capable of measuring energy of a radiation photon incident on the detector. The PCCT device presents a medical image including information more than information presented with conventional CT devices, e.g., a medical image divided into energy components.

Note that to measure energy of the radiation photon with the photon counting type detector, it is necessary to calibrate the relationship between detector output as output from the photon counting type detector and photon energy as the energy of the radiation photon incident on the photon counting type detector. Further, in the photon counting type detector, when a large number of radiation photons are incident per unit time, plural radiation photons may be erroneously detected as a single radiation photon having high photon energy. The phenomenon which causes this erroneous detection is called pile up. Since the pile up causes an inaccurate medical image, it is necessary to perform appropriate pile up correction.

Japanese Patent No. 6386997 discloses a correction method to improve the accuracy of pile up correction. More specifically, a pile up event is corrected based on a synthetic spectrum, generated by changing a parameter vector relating to a pile up event probability and X-ray detector dead time such that the difference with respect to a measurement spectrum is lower than a threshold value.

However, in Japanese Patent No. 6386997, upon generation of the synthetic spectrum by changing the parameter vector, it is necessary to prepare an incident spectrum and to change an incident counting rate. In some cases, the number of measurement times of calibration data used in the pile up correction is increased.

SUMMARY OF THE INVENTION

The present invention has been made in consideration of the above situation, and provides a radiation imaging device capable of reducing the number of measurement times of calibration data used in pile up correction while maintaining the accuracy of pile up correction, and a photon counting type detector calibration method.

The present invention provides a radiation imaging device having a photon counting type detector to output an electric signal corresponding to energy of an incident radiation photon, including: an extraction unit that extracts a component by the number of pile ups from a photon energy spectrum, obtained by detecting a radioactive ray transmitted through a calibration member, formed by combining plural basal substances having different radiation attenuation coefficients, with the photon counting type detector; and a synthesis unit that generates a calibrated equivalent spectrum to be collated with an imaging spectrum obtained by imaging a subject by synthesizing the components by the number of pile ups based on the imaging spectrum.

Further, the present invention provides a photon counting type detector calibration method to output an electric signal corresponding to energy of an incident radiation photon, including: an extraction step of extracting a component by the number of pile ups from a photon energy spectrum of a radioactive ray transmitting through a calibration member, formed by combining plural basal substances having different radiation attenuation coefficients; and a synthesis step of generating a calibrated equivalent spectrum to be collated with an imaging spectrum obtained by imaging a subject by synthesizing the components by the number of pile ups based on the imaging spectrum.

According to the present invention, it is possible to provide a radiation imaging device capable of reducing the number of measurement times of calibration data used in pile up correction while maintaining the accuracy of pile up correction and a photon counting type detector calibration method.

BRIEF DESCRIPTION OF THE DRAWINGS

FIGS. 3A and 3B are diagrams explaining pile up;

FIGS. 7A to 7I are diagrams showing examples of material spectrum, Q component spectrum, and normalized spectrum.

DETAILED DESCRIPTION OF THE PREFERRED EMBODIMENTS

Hereinbelow, an embodiment of the present invention will be described with reference to drawings. A radiation imaging device according to the present invention is applied to a device having a radiation source and a photon counting type detector. In the following explanation, the radioactive ray is an X-ray, and the radiation imaging device is an X-ray CT device.

Figure 1:
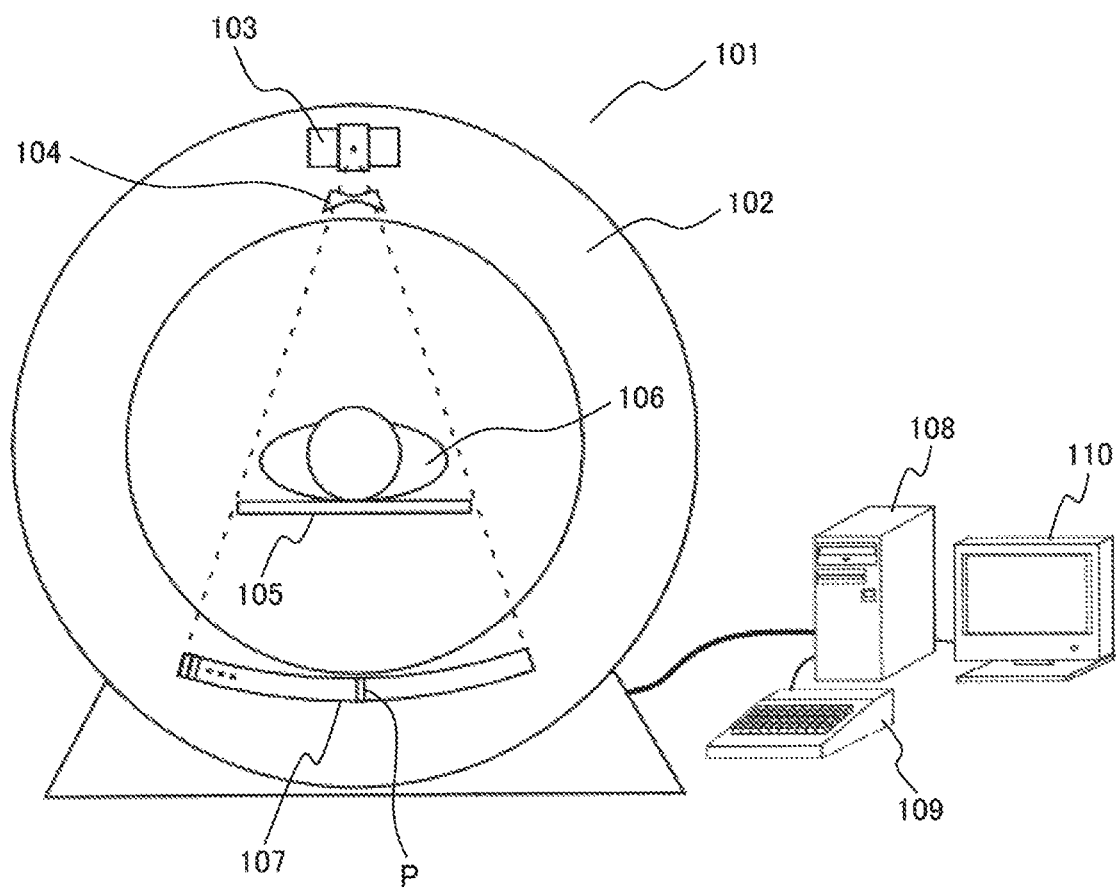
FIG. 1 illustrates the entire configuration of an X-ray CT device.

FIG. 1 illustrates the entire configuration of an X-ray CT device 101 according to the present embodiment. The X-ray CT device 101 has a gantry 102, an X-ray tube 103, a bowtie filter 104, a bed 105, a detector panel 107, an arithmetic unit 108, an input unit 109, and a display device 110. The subject 106 is irradiated with an X-ray emitted from the X-ray tube 103, shaped with the bowtie filter 104 in a beam shape appropriate to the size of the subject 106. The X-ray transmitted through the subject 106 is detected with the detector panel 107. The X-ray tube 103 and the detector panel 107 are attached, oppositely to each other with the subject 106 between them, to the gantry 102. The X-ray tube 103 and the detector panel 107 rotate around the subject 106 by rotation driving with the gantry 102. Along with the rotation driving with the gantry 102, the x-ray irradiation from the X-ray tube 103 and X-ray measurement with the detector panel 107 are repeated, so that projection data is obtained at various projection angles. The arithmetic unit 108 performs image reconstruction processing on the obtained projection data, then a tomographic image of the subject 106 is generated and displayed on the display device 110. Further, when the projection data is obtained while the bed 105 carrying the subject 106 and the gantry 102 relatively move in a body axis direction of the subject 106, a volume image of the subject 106 is generated. Note that the quantity of the X-ray emitted from the X-ray tube 103, the rotational speed of the gantry 102, the speed of the relative movement between the gantry 102 and the bed 105 are set based on scan conditions inputted by an operator via the input unit 109. Further, the arithmetic unit 108 has a hardware configuration similar to that of a regular computer. The arithmetic unit 108 has a CPU (Central Processing Unit), a memory, an HDD (Hard Disk Drive), and the like. The arithmetic unit 108 performs correction processing on the projection data and the like, and controls the respective constituent elements.

The detector panel 107 is configured by arranging plural detector pixels P in an arc shape around an X-ray focus of the X-ray tube 103 as a center. The detector pixel P is a photon counting type detector for measurement of the energy of an incident X-ray photon (photon energy). The detector pixel P outputs a measurement result corresponding to the photon energy.

Next, the output waveform of the photon counting type detector and photon energy spectrum will be described by using FIGS. 2A and 2B. FIG. 2A shows the example of the output waveform of the photon counting type detector. In the figure, the horizontal axis indicates time, and the longitudinal axis indicates the output from the photon counting type detector, i.e., the detector output. In the photon counting type detector, a pulse output 201 occurs upon incidence of an X-ray photon during dead time T. The peak value of the pulse output 201 is proportional to the photon energy. FIG. 2A shows the pulse outputs 201 upon incidence of three types of X-ray photons having different photon energy. A pulse output 201L occurs upon incidence of an X-ray photon having low photon energy; a pulse output 201M occurs upon incidence of an X-ray photon having intermediate photon energy; and a pulse output 201H occurs upon incidence of an X-ray photon having high photon energy. That is, by dividing the detector output with a predetermined threshold value, it is possible to discriminate the incident X-ray photons in N types of photon energy. In FIG. 2A, with three threshold values th1 to Th3, the incident X-ray photons are discriminated into three types of energy ranges, i.e., a range from Th1 to Th2, a range from Th2 to Th3, and a range from Th3. The discriminated energy range is also called an energy bin.

Figure 2B:
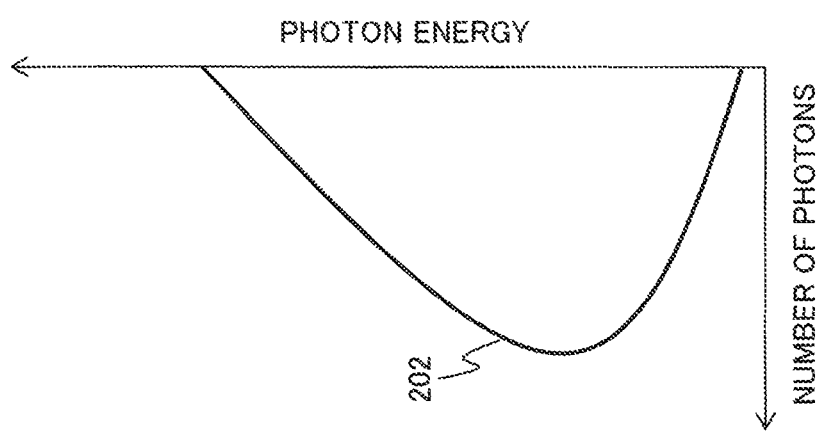
FIGS. 2A and 2B are examples of output waveform of a photon counting type detector and a photon energy spectrum.
Figure 2A:
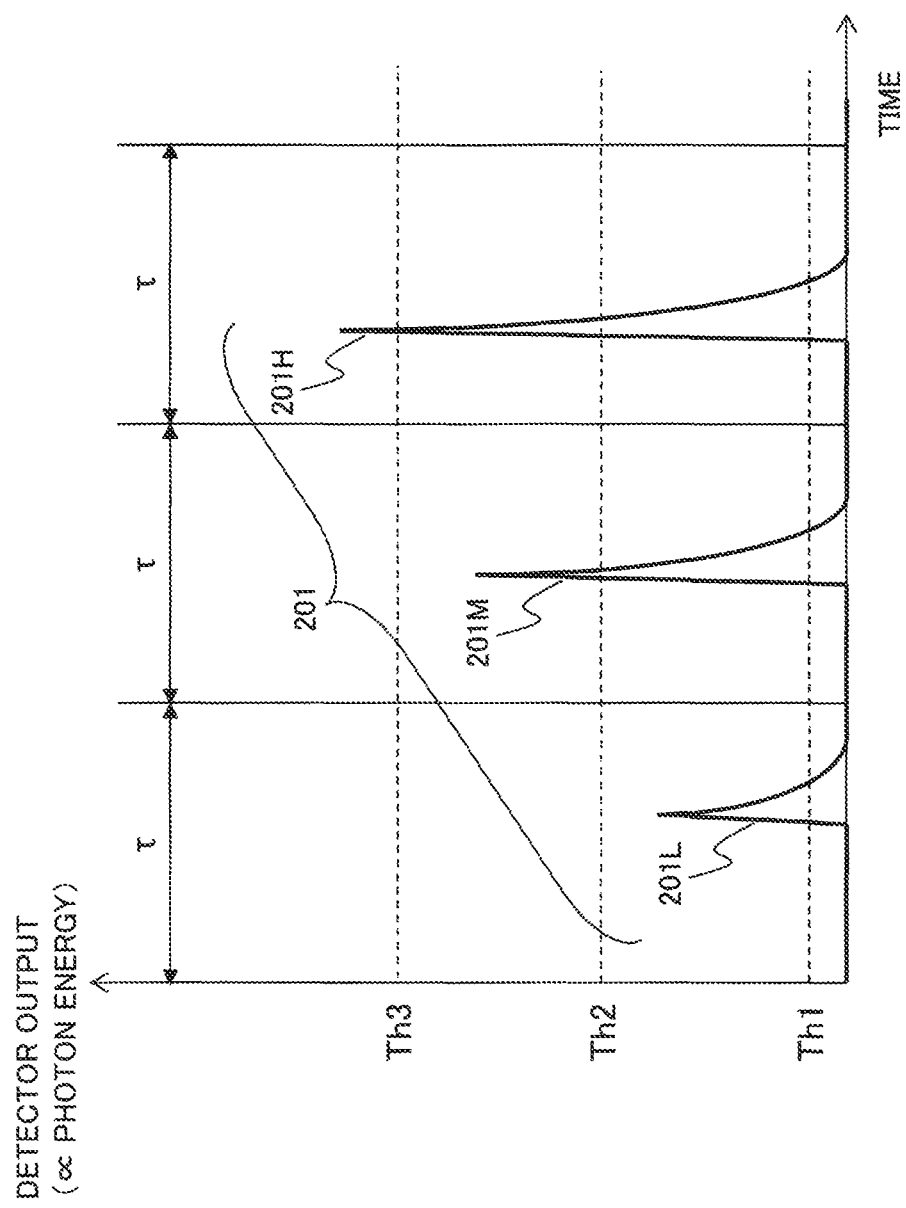

FIG. 2B shows an example of frequency distribution of the X-ray photons with respect to the respective energy bins generated by continuing the measurement as shown in FIG. 2A for constant time, i.e., a photon energy spectrum 202. In the X-ray CT device having the photon counting type detector, the photon energy spectrums in the respective elements of the projection data of the subject 106 are obtained. Accordingly, it is possible to generate a medical image divided into plural energy components and to decompose the subject 106 into basal substances. Note that to measure the X-ray photon energy with the photon counting type detector, it is necessary to calibrate the relationship between the detector output and the photon energy, and to perform pile up correction.

The pile up will be described by using FIGS. 3A and 3B. When the number of X-ray photons incident per unit time is large, the incident plural X-ray photons may be erroneously detected as a single X-ray photon in some cases. The phenomenon which causes this erroneous detection is called pile up. FIG. 3A shows an example of the pile up. In the example, two X-ray photons enter during the dead time τ and first pulse output 301 and second pulse output 302 occur. In FIG. 3A, the first pulse output 301 and the second pulse output 302 are pulse outputs caused with the X-ray photons having different photon energy; however, the pulse outputs 301 and 302 are detected as a single X-ray photon having Th3 or higher photon energy. That is, since the first pulse output 301 is not detected, the number of X-ray photons having photon energy within the range from Th2 to Th3 is reduced. Further, when time T1 and time T2 at which the plural X-ray photons enter are close to each other, the peak values of the respective pulse outputs are superposed and detected. That is, even though the two X-ray photons having photon energy within the range from Th2 to Th3 enter, the number of X-ray photons is reduced, and the X-ray photon having the photon energy of Th3 or higher is erroneously detected. This erroneous detection distorts the photon energy spectrum 202.

FIG. 3B shows an example of the photon energy spectrum 303 including pile up. As shown in FIG. 3B, in the photon energy spectrum 202, which is distorted but not corrected, the number of comparatively-low energy X-ray photons is reduced due to pile up, and the number of comparatively-high energy X-ray photons is increased. The distortion of the photon energy spectrum 202 differs in accordance with the number of superposition of the pulse output 201 during the dead time τ. Hereinafter, the number of superposition of the pulse output 201 during the dead time τ will be referred to as the number Q of pile ups. When no pile up occurs, Q=0 holds.

Figure 4:
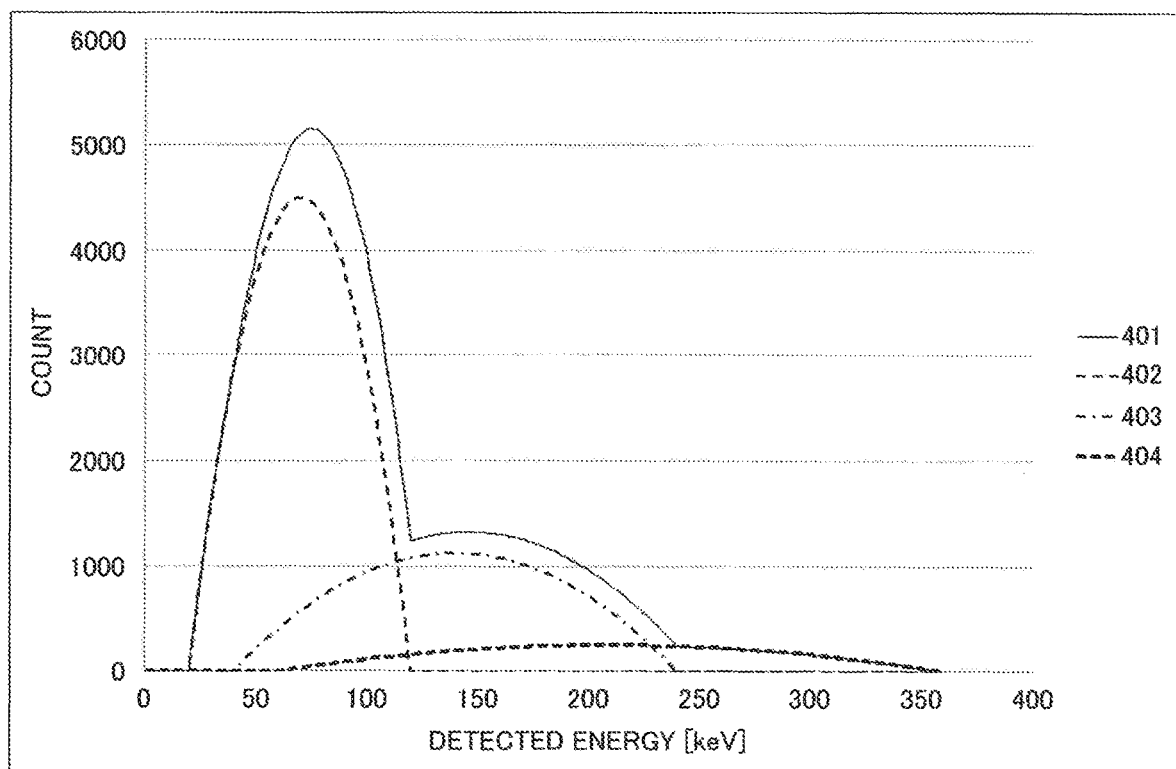
FIG. 4 is a diagram explaining components of the number of pile ups.

The components of the number of pile ups will be described by using FIG. 4. When pile up occurs, the pulse outputs 201 upon incidence of plural X-ray photons are superposed and detected. Then the photon energy range of the photon energy spectrum is widened in correspondence with the number Q of pile ups. That is, as shown in FIG. 4, with respect to a Q=0 component 402 as a photon energy spectrum when Q=0 holds, in a Q=1 component 403, the photon energy range is widened such that the maximum photon energy is twice. In a Q=2 component 404, the photon energy range is widened such that the maximum photon energy is three times. The sum of the respective spectrum components is measured with the counting type detector as a measured spectrum 401.

Note that the ratio of the component by the number Q of pile ups is obtained with Poisson distribution (Q|nτ). More specifically, it is obtained with the following expression.

$$P(Q|n\tau)=(n\tau)^Q \cdot \exp(-n\tau)/Q! \qquad \text{(Expression 1)}$$

where n is an X-ray photon incidence, τ is dead time of the photon counting type detector, and Q! is a factorial of Q. As the incidence rate n is not directly measured, it is calculated as follows. First, a measurement rate m is calculated from the number M of measured photons as the number of photons measured during measurement time τ with the following expression.

$$m = M/T \quad \text{(Expression 2)}$$

Then on the assumption that the photon counting type detector conforms to a non-paralyzed model, the incidence rate n is calculated by using the measurement rate m and the following expression.

$$n = m/(1-m\tau) \quad \text{(Expression 3)}$$

The number of photons by the number Q of pile ups M(Q) is obtained with M·P(Q|nτ).

In the present embodiment, the component by the number Q of pile ups is extracted from the measured spectrum 401 obtained by detecting the X-ray transmitted through a calibration member. The extracted respective components are synthesized based on an imaging spectrum as a photon energy spectrum upon imaging of the subject 106, so as to generate a calibrated equivalent spectrum as a photon energy spectrum to be collated with the imaging spectrum. Note that the calibration member is configured by combining plural basal substances having different X-ray attenuation coefficients.

Figure 5:
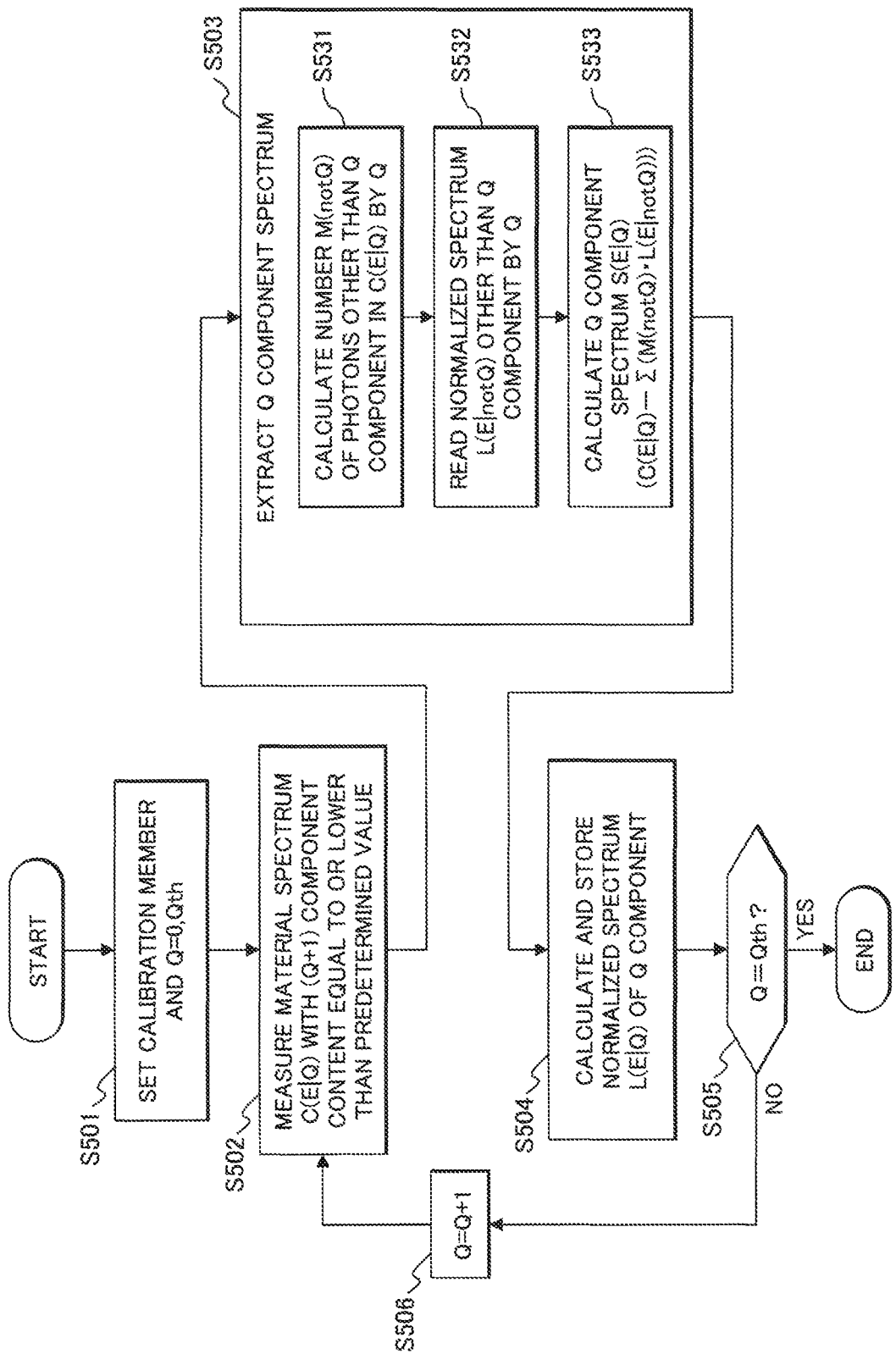
FIG. 5 is a flowchart showing an example of the flow of processing to extract the components by the number of pile ups.

The flow of processing to extract the component by the number Q of pile ups from a material spectrum as a measured spectrum of the calibration member will be described by using FIG. 5.

(S501)

The calibration member 601 is set in the X-ray CT device 101. The number Q of pile ups is initialized (Q=0). A threshold value Qth of the number of pile ups is set. The threshold value Qth is set in correspondence with an upper limit value of the extracted component by the number Q of pile ups. For example, when the extraction is performed up to the Q=2 component, the operator sets the threshold value via the input unit 109 to Qth=2. The values of the number Q of pile ups and the threshold value Qth are stored in the arithmetic unit 108.

Figure 6:
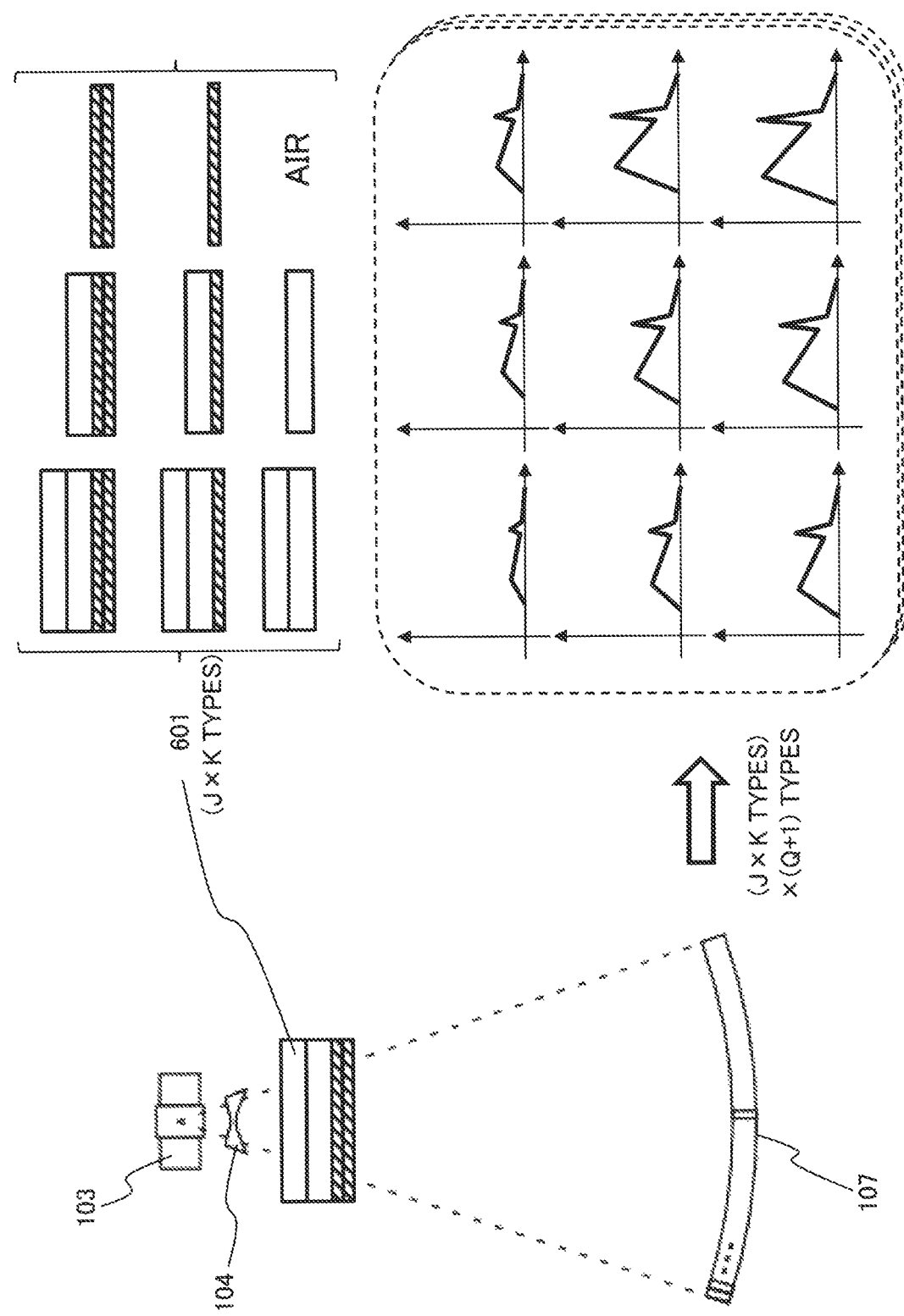
FIG. 6 illustrates measurement of a material spectrum of a calibration member.

The calibration member 601 will be described by using FIG. 6. The calibration member 601 is a member configured by combining plural basal substances having different X-ray attenuation coefficients such as acrylic plate and aluminum plate. Plural plates having different thicknesses may be used by basal substance. For example, assuming that the acrylic plate has J types of thicknesses and the aluminum plate has K types of thicknesses, J×K types of calibration members 601 are used. At the present step, one of the J×K types of calibration members 601 is set. At S502, the material spectrum as a photon energy spectrum of the X-ray transmitted through the calibration member 601 is measured.

(S502)

A material spectrum C(E|Q) is measured with an X-ray amount set such that the (Q+1) component content is equal to or lower than a predetermined value. Note that E is the photon energy. The predetermined value is set such that an upper component in which the number of pile ups larger than the number of pile ups of the (Q+1) component, i.e., the Q component extracted at S503, is negligible. For example, the predetermined value is set to 0.1%. Note that to improve the correction accuracy, the predetermined value is set to a comparatively small value. To reduce the measurement time, the predetermined value is set to a comparatively large value. Further, the predetermined value may be set by the operator via the input unit 109. Otherwise the predetermined value may be set by reading a previously-determined value with the arithmetic unit 108.

The (Q+1) component content is calculated by using the (Expression 1). For example, when Q=0 holds, the (Q+1) component content is P(1|nτ). Accordingly, the arithmetic unit 108 calculates nτ when the P(1|nτ) is a predetermined value, e.g., equal to or lower than 0.1%, then calculates an X-ray photon incident rate n by using the previously obtained dead time τ. As the dead time τ, a value measured by detector pixel P may be used, or an average value of the measured values of all the detector pixels P may be used. Then the material spectrum C(E|Q) is measured with the X-ray amount at the calculated incident rate n.

FIG. 7A shows an example of the material spectrum C(E|Q) when Q=0 holds. Note that the X-ray tube voltage is 120 kV. FIG. 7B shows an example of the material spectrum C(E|Q) when Q=1 holds. FIG. 7C shows an example of the material spectrum C(E|Q) when Q=2 holds. In these cases, the upper component is negligible.

(S503)

The arithmetic unit 108 extracts the Q component spectrum from the material spectrum C(E|Q) measured at S502. Steps S531 to S533 to be described later show the flow of more detailed processing. The arithmetic unit 108, by performing S503, functions as an extraction unit to extract the component by the number Q of pile ups from the photon energy spectrum of the X-ray transmitted through the calibration member 601. Note that only when Q=0 holds, the material spectrum C(E|Q) is the Q component spectrum, and the steps S531 to S533 are skipped. That is, the material spectrum C(E|Q=0) becomes the photon energy spectrum of the Q=0 component. The photon energy spectrum of the Q=0 component shown in FIG. 7D is the same as that in FIG. 7A.

(S531)

The arithmetic unit 108 calculates the number M(notQ) of photons of the component other than the Q component in the material spectrum C(E|Q) by the number Q of pile ups. Note that notQ means respective components other than the Q component. Since the upper component in the material spectrum C(E|Q) is negligible, the number M(notQ) of photons is calculated regarding lower components having a smaller number of pile ups than the number of pile ups in the extracted Q component. The number M(notQ) of photons is calculated by using the following expression.

$$M(\text{not}Q) = M \cdot P(\text{not}Q|n\tau) \quad \text{(Expression 4)}$$

Note that the number M of measured photons is obtained by calculation of the number of all the photons by integrating the number of photons in the area of the material spectrum C(E|Q), i.e., by photon energy E.

(S532)

The arithmetic unit 108 reads a normalized spectrum of the component other than the Q component L(E|notQ) by the number Q of pile ups. Since the read normalized spectrum L(E|notQ) is the normalized spectrum of the lower component, it is already calculated at S504 of the previous loop and is stored in the arithmetic unit 108.

(S533)

The arithmetic unit 108 calculates a Q component spectrum S(E|Q) by using the following expression.

$$S(E|Q) = C(E|Q) - S(\text{not}Q) \cdot L(E|\text{not}Q)) \quad \text{(Expression 5)}$$

With the (Expression 5), the Q component spectrum S(E|Q) is extracted by subtracting the photon energy spectra of the respective lower components from the material spectrum C(E|Q). Note that M(notQ) is photon amount information of the respective lower components. L(E|notQ) is shape information of the photon energy spectra of the respective lower components.

FIG. 7E shows an example of the Q component spectrum S(E|Q) when Q=1 holds. The Q=0 component as a lower component is subtracted from the material spectrum C(E|Q) when Q=1 holds shown in FIG. 7B, thus the Q=1 component is extracted. Further, in an example of the Q component spectrum S(E|Q) when Q=2 holds shown in FIG. 7F, the Q=0 and Q=1 components as lower components are respectively subtracted from the material spectrum C(E|Q) when Q=2 holds shown in FIG. 7C, thus the Q=2 component is extracted.

(S504)

The arithmetic unit 108 calculates the normalized spectrum L(E|Q) from the Q component spectrum S(E|Q) extracted at S503. More specifically, the arithmetic unit 108 calculates the normalized spectrum L(E|Q) by integrating the number of photons in the area of the Q component spectrum S(E|Q), i.e., by photon energy E, to calculate the number of all the photons, and dividing the number of photons by photon energy E by the number of all the photons. The calculated normalized spectrum L(E|Q) is stored in the arithmetic unit 108.

FIG. 7G shows an example of the normalized spectrum L(E|Q) when Q=0 holds. The normalized spectrum L(E|Q) in FIG. 7G has the same shape as the shape of the photon energy spectrum of the Q=0 component shown in FIG. 7D, and is normalized such that the area is 1. Further, the normalized spectrum L(E|Q) when Q=1 and Q=2 hold respectively shown in FIG. 7H and FIG. 7I also have the same shape of the shape of the respective photon energy spectra shown in FIG. 7E and FIG. 7F and normalized such that the area is 1.

(S505)

The arithmetic unit 108 determines whether or not the value of Q is the threshold value Qth. When the value of Q is the threshold value Qth, the flow of processing ends. When the value of Q is not the threshold value Qth, the process proceeds to S506.

(S506)

The arithmetic unit 108 adds 1 to Q thus updates the value of Q, and returns the process to S502. The step S502 is performed via the present step until the value of Q becomes the threshold value Qth. Regarding one calibration member 601, measurement is performed (Qth+1) times. For example, when extraction is performed up to the Q=2 component, since Qth=2 holds, the material spectrum C(E|Q) is measured three times.

With the flow of processing described above, the normalized spectrum by Q component L(E|Q) is calculated and stored. At this time, it is possible to limit the number of times of the measurement using the respective calibration members 601 to a value obtained by adding 1 to the number of extracted components. Note that the stored normalized spectrum by Q component L(E|Q) is also referred to as a pile up template. The pile up template is obtained by type of the calibration member 601.

Figure 8:
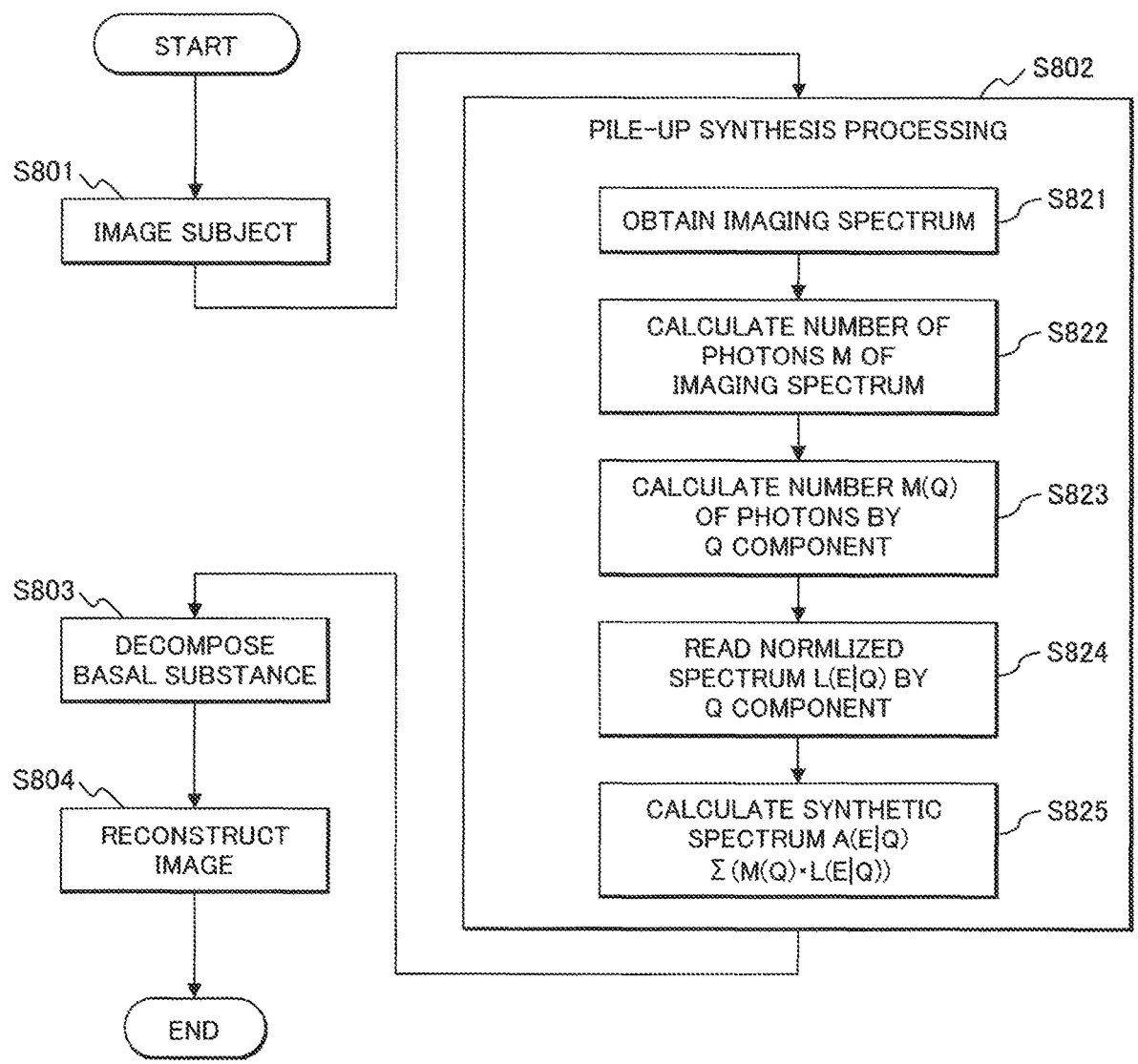
FIG. 8 is a flowchart showing an example of the flow of processing to synthesize the components by number of pile ups.

Next, one example of the flow of processing to generate a calibrated equivalent spectrum, to be collated with the imaging spectrum as a photon energy spectrum obtained by imaging of the subject, by synthesizing the components by the number Q of pile ups, will be described by using FIG. 8.

(S801)

The X-ray CT device 101 performs imaging on the subject 106. That is, the respective detector pixels P of the detector panel 107 obtain an imaging spectrum as a photon energy spectrum of the X-ray transmitted through the subject 106 at various projection angles.

(S802)

The arithmetic unit 108 generates a calibrated equivalent spectrum as a photon energy spectrum to be collated with the imaging spectrum obtained at S801 by pile-up synthesis processing. Steps S821 to S825 to be described later show the flow of more detailed processing. The arithmetic unit 108, by performing S802, functions as a synthesis unit to synthesize the components by the number Q of pile ups based on the imaging spectrum.

(S821)

The arithmetic unit 108 obtains the imaging spectrum upon imaging of the subject 106 at S801.

(S822)

The arithmetic unit 108 calculates the number M of measured photons of the imaging spectrum. More specifically, the arithmetic unit 108 calculates the number M of measured photons of the imaging spectrum by integrating the number of photons in the area of the imaging spectrum, i.e., by photon energy E, to calculate the number of all the photons.

(S823)

The arithmetic unit 108 calculates the number M(Q) of photons by Q component. More specifically, the respective numbers M(Q) of photons are calculated by multiplying P(Q|nτ), obtained by the number Q of pile ups by substituting the number M of measured photons, the X-ray photon incident rate n obtained from the (Expression 2) and the (Expression 3), and the previously obtained dead time τ into the (Expression 1), by the number M of measured photons.

(S824)

The arithmetic unit 108 reads the pile up template L(E|Q) by type of the calibration member 601.

(S825)

The arithmetic unit 108 calculates a synthetic spectrum A(E) by using the following expression.

$$A(E)=S(M(Q)) \cdot L(E|Q)) \quad \text{(Expression 6)}$$

With the (Expression 6), the number M(Q) of photons is multiplied by the normalized spectrum L(E|Q) by the number Q of pile ups, then by adding the products, the synthetic spectrum A(E) is calculated. The calculated synthetic spectrum A(E) becomes the calibrated equivalent spectrum as a photon energy spectrum to be collated with the imaging spectrum. The calibrated equivalent spectrum is calculated by type of the calibration member 601, and a map of the calibrated equivalent spectra as shown in the lower right part of FIG. 6 is formed.

(S803)

The arithmetic unit 108 decomposes the basal substances by collating the imaging spectrum obtained at S801 with the map of the calibrated equivalent spectra and generates projection data by basal substance. More specifically, a calibrated equivalent spectrum most similar to the imaging spectrum is selected from the map of the calibrated equivalent spectra. Then combinations of thicknesses of the basal substances corresponding to the selected calibrated equivalent spectrum are extracted. Then from the extracted combinations of thicknesses of the basal substances, projection data is generated by basal substance. Or, it may be configured such that plural calibrated equivalent spectra similar to the imaging spectrum are selected from the map of the calibrated equivalent spectra, interpolation processing is performed on the respective thicknesses of the basal substances corresponding to the selected calibrated equivalent spectra, and a combination of thicknesses of the basal substances is extracted.

(S804)

The arithmetic unit 108 performs image reconstruction processing on the projection data by basal substance decomposed at S803. As a result of the image reconstruction processing, a tomographic image is generated by basal substance.

With the flow of processing described above, it is possible to generate a calibrated equivalent spectrum to be collated with an imaging spectrum as a photon energy spectrum obtained by imaging of a subject, based on the pile up template L(E|Q), with high accuracy. Further, it is possible to accurately generate a tomographic image by basal substance. Further, the pile up template L(E|Q) is obtained by measurement, the number of times of which corresponds to a value obtained by adding 1 to the number of extracted components. Accordingly, it is possible to reduce the number of measurement times of calibration data in comparison with a case where measurement is required each time the incident counting rate is changed.

The embodiment of the radiation imaging device according to the present invention has been described as above. Note that the radiation imaging device according to the present invention is not limited to the above embodiment, and may be embodied with modification of the constituent elements within a range not departing from the subject matter of the invention. Further, the plural constituent elements disclosed in the above-described embodiment may be arbitrarily combined. Further, some constituent elements may be deleted from all the constituent elements shown in the above-described embodiment.

REFERENCE SIGNS LIST

101: X-ray CT device, 102: gantry, 103: X-ray tube, 104: bowtie filter, 105: bed, 106: subject, 107: detector panel, 108: arithmetic unit, 109: input unit, 110: display device, 201: pulse output, 201L: pulse output when photon energy is low, 201M: pulse output when photon energy is intermediate, 201H: pulse output when photon energy is high, 202: photon energy spectrum, 301: first pulse output, 302: second pulse output, 303: photon energy spectrum including pile up, 401: measured spectrum, 402: Q=0 component, 403: Q=1 component, 404: Q=2 component, and 601: calibration member.

What is claimed is:

1. A radiation imaging device, comprising:
a photon counting type detector to output an electric signal corresponding to energy of an incident radiation photon;
a calibration member including a plurality of basal substances having different radiation attenuation coefficients;
an extraction unit that extracts a component by a number of pile ups from a photon energy spectrum, obtained by detecting a radioactive ray transmitted through the calibration member with the photon counting type detector; and
a synthesis unit that generates a calibrated equivalent spectrum to be collated with an imaging spectrum obtained by imaging a subject by synthesizing a plurality of components by the number of pile ups based on the imaging spectrum;
wherein the extraction unit calculates the extracted component by using a material spectrum as a photon energy spectrum measured so as to make a content of a higher component, with a larger number of pile ups than the number of pile ups of the extracted component, equal to or lower than a predetermined value.

2. The radiation imaging device according to claim 1, wherein the extraction unit calculates the extracted component by subtracting a lower component with the number of pile ups smaller than the number of pile ups of the extracted component from the material spectrum.

3. The radiation imaging device according to claim 1, wherein the extraction unit stores a normalized spectrum obtained by normalizing the component by the number of pile ups.

4. The radiation imaging device according to claim 3, wherein the synthesis unit generates the calibrated equivalent spectrum by adding products between the number of photons by component calculated based on the imaging spectrum and the normalized spectrum by component.

5. The radiation imaging device according to claim 1, wherein the calibration member includes an acrylic plate and an aluminum plate.

6. A photon counting type detector calibration method to output an electric signal corresponding to energy of an incident radiation photon, comprising:
obtaining, by a calibration member including a plurality of basal substances having different radiation attenuation coefficients, a photon energy spectrum of a radioactive ray transmitted through the calibration member;
an extraction step of extracting a component by a number of pile ups from the photon energy spectrum of the radioactive ray transmitted through the calibration member; and
a synthesis step of generating a calibrated equivalent spectrum to be collated with an imaging spectrum obtained by imaging a subject by synthesizing a plurality of components by the number of pile ups based on the imaging spectrum;
wherein the extraction step includes calculating the extracted component by using a material spectrum as a photon energy spectrum measured so as to make a content of a higher component, with a larger number of pile ups than the number of pile ups of the extracted component, equal to or lower than a predetermined value.

7. The photon counting type detector calibration method according to claim 6, wherein the calibration member includes an acrylic plate and an aluminum plate.

* * * * *